United States Patent
Lin

(10) Patent No.: US 11,718,822 B2
(45) Date of Patent: Aug. 8, 2023

(54) COMPOSITE SHELL PARTICLE, BIOLOGICAL MATERIAL, AND METHOD OF MANUFACTURING COMPOSITE SHELL PARTICLE

(71) Applicant: ACON-HOLDING INC., New Taipei (TW)

(72) Inventor: Pao-Hung Lin, Taipei (TW)

(73) Assignee: ACON-HOLDING INC., New Taipei (TW)

( * ) Notice: Subject to any disclaimer, the term of this patent is extended or adjusted under 35 U.S.C. 154(b) by 288 days.

(21) Appl. No.: 17/105,534

(22) Filed: Nov. 26, 2020

(65) Prior Publication Data
US 2021/0087524 A1 Mar. 25, 2021

Related U.S. Application Data

(62) Division of application No. 16/373,607, filed on Apr. 2, 2019, now Pat. No. 10,876,093.

(51) Int. Cl.
| | |
|---|---|
| *C12N 1/20* | (2006.01) |
| *C12N 5/00* | (2006.01) |
| *B01J 13/04* | (2006.01) |
| *B01J 13/12* | (2006.01) |
| *B01J 13/14* | (2006.01) |

(52) U.S. Cl.
CPC .......... *C12N 5/0012* (2013.01); *B01J 13/043* (2013.01); *B01J 13/12* (2013.01); *B01J 13/14* (2013.01); *C12N 1/20* (2013.01); *C12N 5/0025* (2013.01); *C12N 2500/24* (2013.01); *C12N 2500/72* (2013.01); *C12N 2500/74* (2013.01)

(58) Field of Classification Search
CPC ........ C12N 1/20; C12N 1/12; C12N 2500/10; C12N 2500/20; C12N 2500/24
See application file for complete search history.

(56) References Cited

FOREIGN PATENT DOCUMENTS

| | | |
|---|---|---|
| JP | 2018090582 | 6/2018 |
| WO | WO-2011141418 A1 * | 11/2011 .............. B01J 23/44 |

OTHER PUBLICATIONS

Lin 2017 "Sodium Tungstate and Sodium Molybdate Hollow Microspheres" ECS J. Solid State Sci. Technol. 6 N3113 (2017) (Year: 2017).*
Lin 2018 "Synthesizing Sodium Tungstate and Sodium Molybdate Microcapsules via Bacterial Mineral Excretion" J. Vis. Exp. (131), e57022, doi:10.3791/57022 (2018). (Year: 2018).*
"Office Action of Japan Counterpart Application", dated Jan. 26, 2021, p. 1-p. 4.

* cited by examiner

*Primary Examiner* — Thane Underdahl
(74) *Attorney, Agent, or Firm* — JCIPRNET

(57) ABSTRACT

A composite shell particle including a composite shell layer is provided. The composite shell layer is a hollow shell, wherein the composite shell layer includes a porous biological layer and a metallic layer. The porous biological layer is composed of an organic substance including a cell wall or a cell membrane of a bacteria or algae. The metallic layer is crosslinked with the porous biological layer to form the composite shell layer. The metallic layer includes at least one metal selected from the group consisting of iron, molybdenum, tungsten, manganese, zirconium, cobalt, nickel, copper, zinc, and calcium, and/or includes at least one selected form the group consisting of metal chelates, metal oxides, metal sulfides, metal chlorides, metal selenides, metal acid salt compounds, and metal carbonate compounds. A method of manufacturing the composite shell particle, and a biological material including the composite shell particle and the applications thereof are also provided.

17 Claims, 7 Drawing Sheets

COMPOSITE SHELL PARTICLE, BIOLOGICAL MATERIAL, AND METHOD OF MANUFACTURING COMPOSITE SHELL PARTICLE

CROSS-REFERENCE TO RELATED APPLICATION

This application is a divisional application of U.S. application Ser. No. 16/373,607, filed on Apr. 2, 2019, now allowed. The entirety of the above-mentioned patent application is hereby incorporated by reference herein and made a part of specification.

BACKGROUND OF THE INVENTION

Field of the Invention

The invention relates to a preparation technique of a nanomaterial, and more particularly, to a composite shell particle, a biological material, and a method of manufacturing the composite shell particle.

Description of Related Art

Organisms such as microorganisms, plants, and animals may all form minerals in nature. The phenomenon of forming inorganic minerals in living organisms may be called biomineralization. The process of biomineralization refers to the participation of cells in the organism, so that inorganic elements in the environment may be selectively precipitated on specific organic matters to form minerals. Biologically-induced mineralization and the biological control of mineralization have been studied by scholars for decades. However, such research is mostly used in the field of environmental protection. At present, the research on the reaction between microorganisms and metals similar to the two kinds of mineralization mentioned above and the development of novel materials are topics worthy of further discussion and research.

SUMMARY OF THE INVENTION

Accordingly, the invention provides a composite shell particle and a method of manufacturing the same, and the composite shell particle may be used to prepare a biological material.

In some embodiments, the composite shell particle of the invention includes a composite shell layer. The composite shell layer is a hollow shell, and the composite shell layer at least includes a porous biological layer and a metallic layer. The porous biological layer is composed of an organic substance including a cell wall or a cell membrane of a bacteria or algae. The metallic layer is crosslinked with the porous biological layer to form the composite shell layer, wherein the metallic layer includes at least one metal selected from the group consisting of iron, molybdenum, tungsten, manganese, zirconium, cobalt, nickel, copper, zinc, and calcium, and/or includes at least one selected form the group consisting of metal chelates, metal oxides, metal sulfides, metal chlorides, metal selenides, metal acid salt compounds, and metal carbonate compounds.

In some embodiments, the method of manufacturing the composite shell particle of the invention includes the following steps. Bacteria or algae cells are co-cultured with a culture medium including a carbon source and a metal raw material for a period of time, and the bacteria or algae cells induces the metal raw material in the culture medium to undergo a redox reaction to produce a wet powder material including a composite shell particle, wherein the metal raw material is composed of a metal compound, and the metal in the metal compound is at least one selected from the group consisting of iron, molybdenum, tungsten, manganese, zirconium, cobalt, nickel, copper, zinc, and calcium, and the metal compound is at least one selected from the group consisting of metal chelates, metal oxides, metal sulfides, metal chlorides, metal selenides, metal acid salt compounds, and metal carbonate compounds. The wet powder material is separated from the culture medium. The wet powder material is dried to obtain a powder material, wherein the powder material includes at least one composite shell particle. The powder material including the composite shell particle is placed in a solution or under vacuum and reacted at 0° C. to 250° C. to enhance the compressive strength of the composite shell particle.

In some embodiments, the invention provides a biological material, the biological material may include the composite shell particle, and the biological material is, for example, an artificial bone material.

Based on the above, the composite shell particle, the biological material, and the method of manufacturing the composite shell particle of the embodiments of the invention are suitable for manufacturing a novel material so that the obtained material has excellent mechanical properties and structural strength. In addition, the composite shell particle of the embodiments of the invention is simple in manufacture, is low in cost, and may be directly applied to industrial production.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

In the present specification, the term "weight percentage" refers to the weight percentage calculated based on the number of moles of carbon in a carbon source.

Figure 1A:
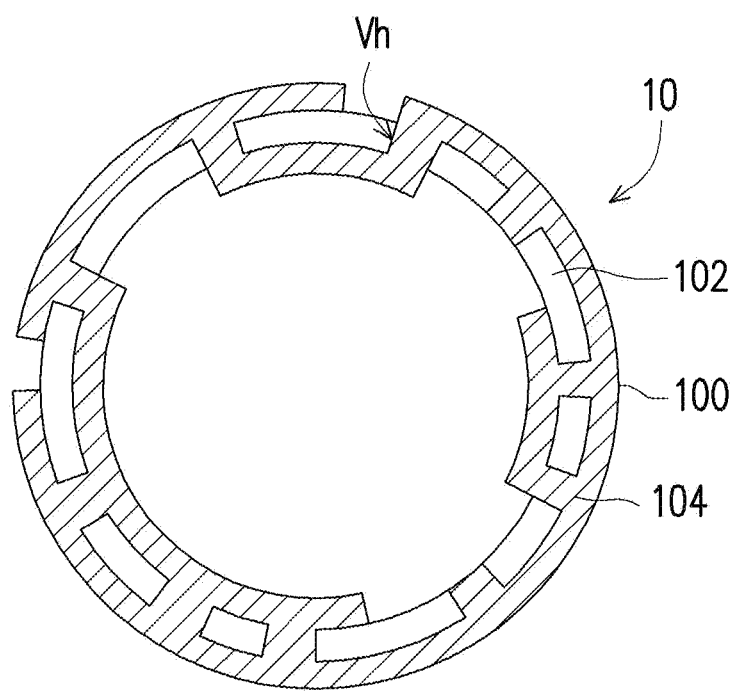
FIG. 1A is a cross sectional view of a composite shell particle according to an embodiment of the invention.
Figure 1B:
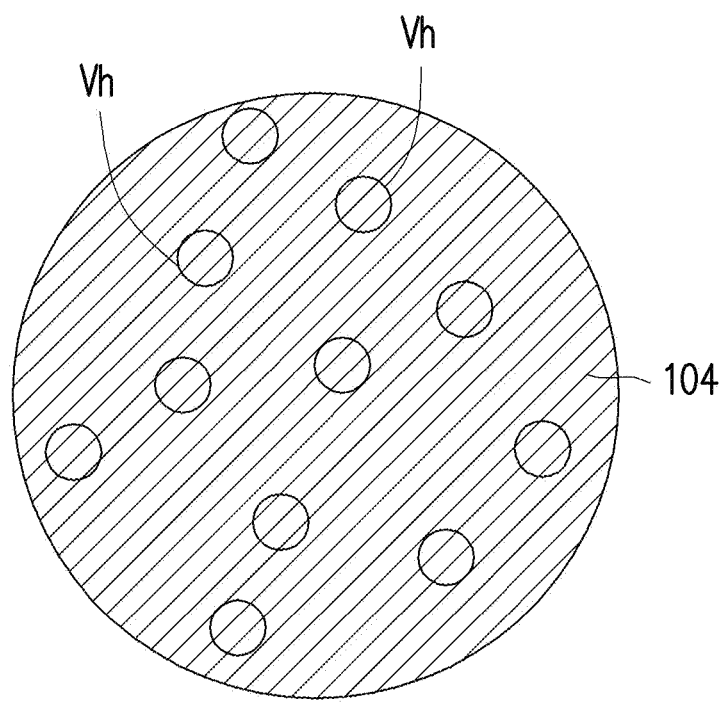
FIG. 1B is a top view of a composite shell particle according to an embodiment of the invention.

Referring to FIG. 1A and FIG. 1B, in some embodiments, a composite shell particle 10 may include a composite shell layer 100. The composite shell layer 100 is a hollow shell and the shell surrounds and defines a housing space in the middle. The composite shell layer 100 includes a porous biological layer 102 and a metallic layer 104 crosslinked with the porous biological layer 102. For example, the metallic layer 104 is crosslinked with the porous biological layer 102 to form the composite shell layer 100. As shown in FIG. 1B, the porous biological layer 102 includes a plurality of pores Vh, and the pores Vh may be irregularly dispersed on the porous biological layer 102, but the invention is not limited thereto. In other embodiments, the pores Vh may also be regularly dispersed on the porous biological layer 102. Furthermore, the metallic layer 104 may pass through the plurality of pores Vh of the porous biological layer 102 to form a crosslinked structure.

The porous biological layer 102 may be composed of an organic substance including a cell wall or a cell membrane of a bacteria or algae, and is, for example, a cell wall composed of cellulose. For example, an organic substance may include only a cell wall or cell membrane of a particular bacteria or algae, or may include a small amount of other carbon-containing organic matter. The weight percentage of the porous biological layer 102 may be 5% to 80% of the composite shell layer 100, and the weight percentage of the porous biological layer 102 in the composite shell layer 100 may be greater than the weight percentage of the metallic layer 104 in the composite shell layer 100. The metallic layer 104 may be composed of at least one of metal chelates, metal oxides, metal sulfides, metal chlorides, metal selenides, metal acid salt compounds, and metal carbonate compounds, or a combination thereof. In some embodiments, the metallic layer 104 may include metal chelates, chlorides, or acid salt compounds or be formed by any of the above or a combination thereof. Moreover, the weight percentage of the metal element contained in the metallic layer 104 may be between 3% and 75% of the composite shell layer 100.

In some embodiments, the porous biological layer 102 may be formed by an organic substance of a cell wall or a cell membrane of a Gram-negative bacteria, or an organic substance of a cell wall or a cell membrane of algae. For example, the porous biological layer 102 may be formed by an organic substance of a cell wall or a cell membrane of a specific bacteria or algae, wherein the specific bacteria or algae includes *Shewanella* sp., *Pantoea* sp., *Pseudomonas aeruginosa, Bacillus subtilis, Crustose coralline* algae, or the like, or a mixture thereof, but is not limited thereto. In some embodiments, the metallic layer 104 may be formed by at least one metal such as iron, molybdenum, tungsten, manganese, zirconium, cobalt, nickel, copper, zinc, or calcium and/or metal chelates, metal oxides, metal sulfides, metal chlorides, metal selenides, metal acid salt compounds, or metal carbonate compounds of a metal above or any combination thereof, and may also be formed by other alternative metal compounds. In some embodiments, the metal is iron, and the metallic layer 104 includes a chelate of EDTA and iron (Fe-EDTA coordination complex), iron oxide, ferric citrate, or iron chloride. In some embodiments, the metallic layer 104 may include a salt compound such as a manganate compound or a cuprate compound, or include a compound such as copper chloride, zinc chloride, copper oxide, or zinc oxide.

In some embodiments, the porous biological layer 102 and the metallic layer 104 may be suitably used together according to the requirements of the application and based on the nature of the material. For example, when the porous biological layer 102 is formed by an organic substance of a cell wall or a cell membrane of *Shewanella* sp., the metallic layer 104 may be formed by a chelate of EDTA and iron, ferric citrate, iron chloride, iron oxide, a manganate compound, or a cuprate compound. Alternatively, when the porous biological layer 102 is formed by a cell wall or a cell membrane of *Pantoea* sp., the metallic layer 104 may be formed by a chelate of EDTA and iron or iron chloride or iron oxide. However, the invention is not limited thereto.

In some embodiments, the interior of the composite shell layer 100 is hollow and has a particular thickness. The "thickness" mentioned herein refers to the smallest distance between any point on the inner surface of the composite shell layer and any point on the outer surface thereof. In some embodiments, the composite shell layer 100 may have a thickness between 5 nm and 60 nm. In some embodiments, the composite shell layer 100 may have a thickness between 20 nm and 40 nm. Moreover, in some other embodiments, the composite shell layer 100 may be a hollow shell.

In some embodiments, the composite shell layer 100 may be a hollow sphere-shaped shell. This spherical composite shell layer 100 has a specific diameter. In terms of a concentric sphere between the inner and outer surfaces of the spherical composite shell layer 100, the "diameter" herein refers to the diameter of a concentric sphere located between the inner and outer surfaces of the spherical composite shell layer 100. Also, the shortest distance from any point on the inner surface of the composite shell layer 100 and any point on the outer surface of the composite shell layer 100 to any point on the surface of the above concentric sphere is the same. In some embodiments, the hollow sphere-shaped composite shell layer 100 may have a diameter between 0.2 microns (μm) and 2 microns. In some embodiments, the hollow sphere-shaped composite shell layer 100 may have a diameter of about 1 micron.

Figure 1C:
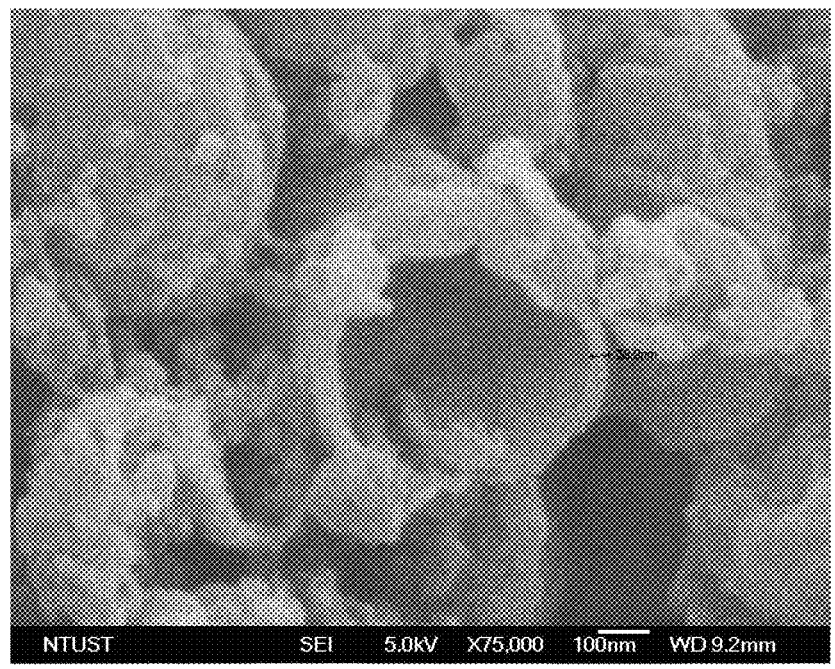
FIG. 1C is an SEM analysis result of a composite shell particle according to an embodiment of the invention.

FIG. 1C is the scanning electron microscope (SEM) analysis result of a composite shell particle of an embodiment of the invention. Referring to the SEM analysis result of FIG. 1C, the composite shell particle of an embodiment of the invention is spherical and has a diameter of about 0.5 microns to 0.6 microns, and the thickness of the composite shell layer is about 38.9 nm. However, the invention is not limited thereto.

In the above embodiments, the composite shell layer 100 is exemplified as spherical, but the invention is not limited thereto. In some other embodiments, the composite shell layer 100 may be a hollow rod-shaped shell. The rod-shaped composite shell layer 100 may include a middle portion and two end portions respectively connected to the middle portion. In particular, the end portions may be dome-shaped. More specifically, the inner circumference and the outer circumference of the two end portions may be respectively connected to the inner circumference and the outer circumference of the two ends of the middle portion. In the case of the portion of largest area of the two dome-shaped ends, the "width" herein refers to the maximum distance between any two points of the line connected by the intermediate points of the minimum distance between any point located on the inner circumference of the portion and any point located on the outer circumference (i.e., the width of the middle portion). For example, if the portion of the largest area of the two end portions is circular, then the width is the diameter of a concentric circle located between the inner circumference and the outer circumference. Further, the shortest distance from any point on the inner circumference of the end portions and any point on the outer circumference to any point on the circumference of the concentric circle is the same. In some embodiments, the thickness of each end portion is not less than 1/73 of the width of the composite shell layer 100, and the thickness of the middle portion is not less than 1/37 of the width of the composite shell layer 100. In some embodiments, the rod-shaped composite shell layer 100 may have a width between 0.2 microns and 2 microns. In some embodiments, the rod-shaped composite shell layer 100 may have a width of 1 micron. In addition, the "length" of the rod-shaped composite shell layer refers to the largest distance between the center points of the smallest distance respectively formed between the apex of the outer surface of the two dome-shaped end portions and the apex of the inner surface. In some embodiments, the rod-shaped composite shell layer 100 may have a length between 1 micron and 10 microns.

Figure 2:
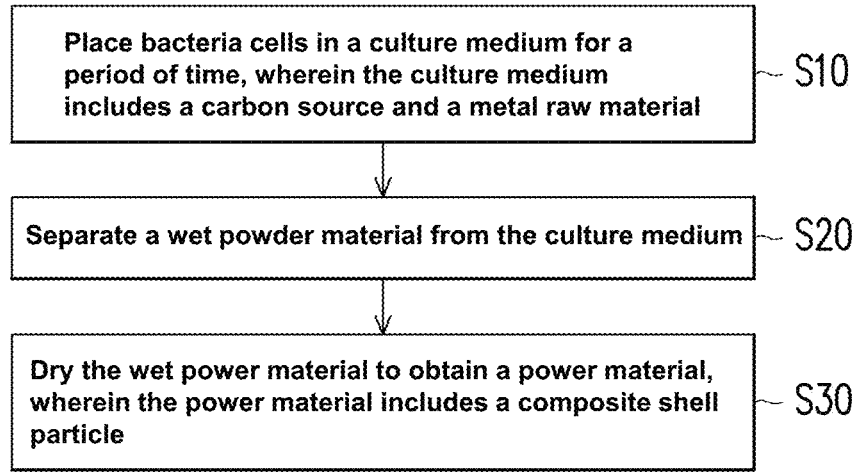
FIG. 2 is a flowchart of a method of manufacturing a composite shell particle according to an embodiment of the invention.

Referring to FIG. 2, in some embodiments, the method of manufacturing the composite shell particle may include the following process (taking bacteria cells as an example). First, bacteria cells are cultured in a culture medium for a period of time (S10). In particular, the culture medium may include a carbon source and a metal raw material. During the culture process, the bacteria cells induce a redox reaction of the metal raw material to produce a wet powder material containing composite shell particles. Next, the wet powder material is separated from the culture medium (S20). Lastly, the wet powder material is dried to obtain a powder material (S30). The obtained powder may be substantially in the form of a dispersed powder or may be aggregated into a solid. In particular, the powder material may include the composite shell particle 10. Further, in some embodiments of step S20, the upper layer of the culture medium may be foamed, and a suspension may be separated from the foam to obtain the wet powder material.

In some embodiments, after obtaining the powder material, the powder material including the composite shell particle 10 is placed in a specific solution or in a vacuum, and a reaction is performed at 0° C. to 250° C. to enhance the compressive strength of the composite shell particle 10. For example, in one embodiment, the composite shell particle 10 is placed in an aqueous solution at 0° C. to 100° C. to undergo a hydration reaction for 3 days to 7 days, wherein the composite shell particles 10 are bonded to each other via the hydration reaction to form a larger structure. For example, a plurality of composite shell particles 10 are bonded to each other to form a centimeter-grade structure.

In another embodiment, the composite shell particle 10 is placed in an organic solution (for example, alcohol), heated to 60° C. to 80° C. and removing the organic solution, and then reacted in a vacuum environment at 150° C. to 250° C. for 4 hours to 24 hours to scorch and crosslink the cellulose of the cell wall in the composite shell particle (e.g., forming a scorched carbon layer) to enhance the compressive strength of the composite shell particle. In some other embodiments, the composite shell particle 10 may also be placed in mineral oil or vegetable oil and heated to 150° C. to 250° C. for 4 hours to 24 hours to scorch and crosslink the cellulose of the cell wall in the composite shell particle to enhance the compressive strength of the composite shell particle. By the above method, the compressive strength of the composite shell particle 10 may be further enhanced. For example, the composite shell particle 10 prepared by the above method may have a compressive strength greater than 6 MPa or greater than 10 MPa. In some embodiments, the composite shell particle 10 may have a compressive strength of 37 MPa or more.

In some embodiments, the bacteria may be a Gram-negative bacteria, such as: *Shewanella* sp., *Pantoea* sp., *Pseudomonas aeruginosa, Bacillus subtilis*, other alternative Gram-negative bacteria, or any combination thereof. More preferably, the bacteria may be *Shewanella* sp., *Pantoea* sp., *Pseudomonas aeruginosa*, or *Bacillus subtilis*. The bacteria or algae used in the culturing step is the source of the components of the porous biological layer in the composite shell layer of the composite shell particle. In some embodiments, the metal raw material may be a metal compound. For example, the metal raw material may be a chelate of a metal such as iron, molybdenum, tungsten, manganese, zirconium, cobalt, nickel, copper, zinc, or calcium, metal oxides, metal sulfides, metal chlorides, metal selenides, metal acid salt compounds, metal carbonate compounds, or other alternative metal compounds. The metal raw material may be used as a source of components for the metallic layer of the composite shell layer. For example, the metallic layer of the composite shell layer may be formed by a metal raw material or a product formed by the redox reaction of the metal raw material.

In some embodiments, suitable bacteria and metal raw materials may be selected to produce the desired powder material according to production requirements. For example, the bacteria in the culture medium may be *Shewanella* sp., and the metal raw material may be a chelate of EDTA and iron or iron chloride or iron oxide. Further, in some embodiments, the concentration of the metal raw material and carbon source in the culture medium may respectively be 0.01 M to 0.25 M. More preferably, the concentration of the metal raw material in the culture medium may be 0.1 M to 0.25 M.

In some embodiments, "carbon source" refers to any carbohydrate-based material that provides a source of energy needed in the culture medium for the growth and reproduction of bacteria and a source of carbon components necessary to synthesize the cells. Any inorganic or organic carbon-containing compounds may be the carbon source that the microorganism may utilize, such as carbon dioxide, carbonate, sugar and sugar derivatives, alcohols, organic acids, lipids, hydrocarbons, aromatic compounds, and the like. For example, glucose, sucrose, starch, fructose, lactose, lactate, formate, pyruvic acid, and/or amino acid may be utilized as the carbon source. In some embodiments, the concentration of the carbon source in the culture medium may be 0.01 M to 0.25 M. Further, in some embodiments, the culture medium may be prepared using any suitable commercially available culture medium formula, such as: Luria broth (LB) culture medium, M9 culture medium, other alternative culture media, or any combination thereof.

Temperature has an important influence on the growth of bacteria, and therefore bacterial culturing may occur at a temperature suitable for growth of the bacteria. In the embodiment of step S10, the bacteria may be placed in a culture medium and cultured under an aerobic environment at 37° C. The culturing time has an effect on the amount of bacteria grown. If the culturing time is too short, then the growth of the bacteria is insufficient, such that the yield of the composite shell particle is poor. In the embodiment of step S10, the bacteria may be cultured in the culture medium for at least 3 days, and more preferably 7 days to 10 days.

In some embodiments, step S20 may also include centrifuging the culture medium or other alternative means to separate a precipitate from the culture medium. In some embodiments, after the precipitate is separated from the culture medium, the precipitate may be subjected to high-frequency oscillation, such as ultrasonic oscillation to pulverize the precipitate. Further, in some embodiments, the precipitate may be washed with a solvent once or repeatedly for twice or more. Various common solvents may be used to wash the precipitate, such as water, ethanol, other alternative solvents, or any combination thereof. For example, RO water, deionized water, or ethanol may be used to wash the precipitate.

Figure 3:
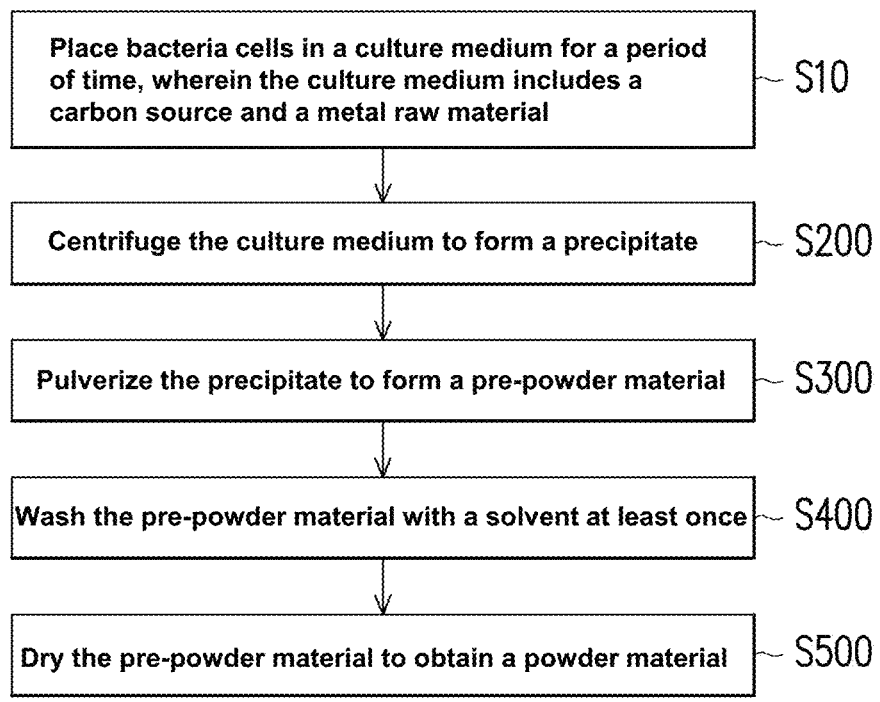
FIG. 3 is a flowchart of a method of manufacturing a composite shell particle according to another embodiment of the invention.

Referring to FIG. 3, in some embodiments, after step S10, the culture medium is centrifuged to form a precipitate (i.e., wet powder material) (S200). Next, the precipitate is pulverized to form a pre-powder material (S300), and the pre-powder material is washed with the solvent at least once (S400). Lastly, the precipitate is dried by ventilation or heating at a suitable temperature (S500) to remove the solvent in the precipitate and to obtain a powder material. Further, in some embodiments, the density of the powder material is 420 kg/m$^2$.

In some embodiments, the amount of the culture medium or metal raw material used in the culturing step may be adjusted such that the composite shell layer of the composite shell particle forms a hollow sphere-shaped shell or a hollow rod-shaped shell. For example, the concentration of sugar (i.e., carbon source) or metal raw material added to the culture medium may be adjusted as compared to a general bacteria culturing process, such that the bacteria undergoes a stress response and a change in appearance. In some embodiments, the use of a high-concentration metal raw material (e.g., 0.1 M to 0.2 M) may promote the occurrence of a stress response and alter the appearance of bacteria in the culture medium. In some embodiments, the change in appearance of the bacteria may cause the cell wall thereof to form a spherical shell or to become rod-shaped shells having two dome-shapes. Accordingly, the obtained composite shell layer may be a hollow sphere-shaped shell or a hollow rod-shaped shell.

In some embodiments, the composite shell layer of the composite shell particle may be further subjected to a treatment such as oxidation, vulcanization, chlorination, or selenization. For example, the metallic layer may form a metal oxide after reacting with oxygen in the environment at a high temperature (for example, 300° C. to 1000° C.) and/or an oxygen-rich environment, and the composite shell layer is mostly formed by a metallic layer that is formed into metal oxide. The metal oxide generally refers to a metal oxide which usually has only a metal element and an oxygen atom, and does not include an acid salt ion or compound containing an oxygen atom of a metal. Alternatively, for example, the oxidized composite shell layer may be vulcanized by mechanical stripping or chemical vapor deposition such that the oxygen atoms of the metal oxide in the metallic layer are replaced by sulfur atoms via a displacement reaction. Here, the composite shell layer is mostly formed by a metallic layer formed into metal sulfide. Similarly, the oxygen atoms of the metallic layer may be chlorinated or selenized by mechanical stripping or chemical vapor deposition, such that the oxygen atoms of the metal oxide in the metallic layer may be replaced by chlorine atoms or selenium atoms via a displacement reaction, such that the composite shell layer is mostly formed by a metallic layer that is formed into metal chloride or selenide. In addition, the characteristic changes of the composite shell layer after a treatment such as oxidation, vulcanization, chlorination, selenization, etc. above may be measured by a general detection method such as Raman spectrum, photoluminescence spectrum, electron microscope, or the like. For example, the energy gap of the metallic layer of the composite shell layer may be measured to be between 1.2 eV and 1.8 eV using photoluminescence spectroscopy.

In some embodiments, the resulting powder material may also be placed in a reactor. Moreover, in a reaction furnace, the powder material is heated for a period of time (i.e., sintered) respectively in a vacuum, oxygen, sulfur vapor (such as: hydrogen sulfide), chlorine vapor (such as: hydrogen chloride), or selenium vapor (such as: hydrogen selenide) at 300° C. to 1000° C. or at a suitable temperature. As such, the composite shell layer of the composite shell particle in the powder material is oxidized, vulcanized, chlorinated, or selenized, such that the metallic layer of the composite shell layer is mostly formed into metal oxides, metal sulfides, or metal selenides. In some embodiments, after the composite shell layer is oxidized, vulcanized, or selenized, the weight percentage of the metallic layer in the composite shell layer is greater than the weight percentage of the porous biological layer in the composite shell layer.

In some embodiments of the invention, a biological material including the composite shell particle is provided. The composite shell particle may provide a biological material with excellent mechanical properties and structural strength. In some embodiments, the biological material is, for example, an artificial bone material, but the invention is not limited thereto. In other embodiments, the composite shell particle may be used for any biological materials that require specific mechanical properties and structural strength. In one embodiment, the artificial bone material is prepared by drying the resulting composite shell particle powder, followed by heating and maintaining under a vacuum environment for a period of time to cause the cellulose in the composite shell particle to crosslink and harden to obtain the enhanced composite shell particle. The enhanced composite shell particle is then grinded into powder and printed into artificial bone material via a conventional 3D printing method.

Experimental Example

In the following experimental example, an EDTA-iron chelate hollow nanosphere composite shell particle is prepared as an example.

In the experimental example of the invention, the composite shell particle was produced by the following procedure. First, *Shewanella* sp. was taken from white shrimp (*Litopenaeus vannamei*). Next, the *Shewanella* sp. was cultured in an LB culture medium for 16 hours in an environment of 37° C. Next, a carbon source (glucose) of about 0.2 M and an EDTA-iron chelate of about 0.2 M were added to the culture medium, and the *Shewanella* sp. was further cultured for 5 days under the same environment. Upon completion of the culturing process, the culture medium was centrifuged and the supernatant was removed to obtain a precipitate. The precipitate was ultrasonically oscillated to pulverize the precipitate. The pulverized precipitate (i.e., pre-powder material) was repeatedly washed with deionized water several times to obtain a powdery and non-sticky product. The powder material was resuspended in ethanol and dried at 40° C. to obtain a powder material including composite shell particles.

Next, the powder material including the composite shell particles was placed in an alcohol and heated to 70° C. for preliminary reaction, and after drying to remove the alcohol, the composite shell particle was reacted at 180° C. for about six hours in a vacuum environment, such that the cellulose of the cell wall in the composite shell particle was scorched and crosslinked to enhance the compressive strength of the composite shell particle. After the reaction was completed, drying was performed in the same manner to obtain a powder material.

The enhanced powder material was compressed into a tablet at a pressure of 10 MPa to perform subsequent qualitative measurement of the sheet-like powder material. First, the volume and weight of the sheet-like powder material were measured to find that the density thereof was 420 kg/m$^2$. In the atmosphere, SEM image analysis of the powder material was performed using a field-emission scanning electron microscope (FESEM) model JEOL JSM-6500F, and energy-dispersive X-ray spectroscopy (EDS) analysis and X-ray diffraction (XRD) analysis were performed. The experimental results are shown in FIG. 4, FIG. 5, and FIG. 6.

Figure 4A:
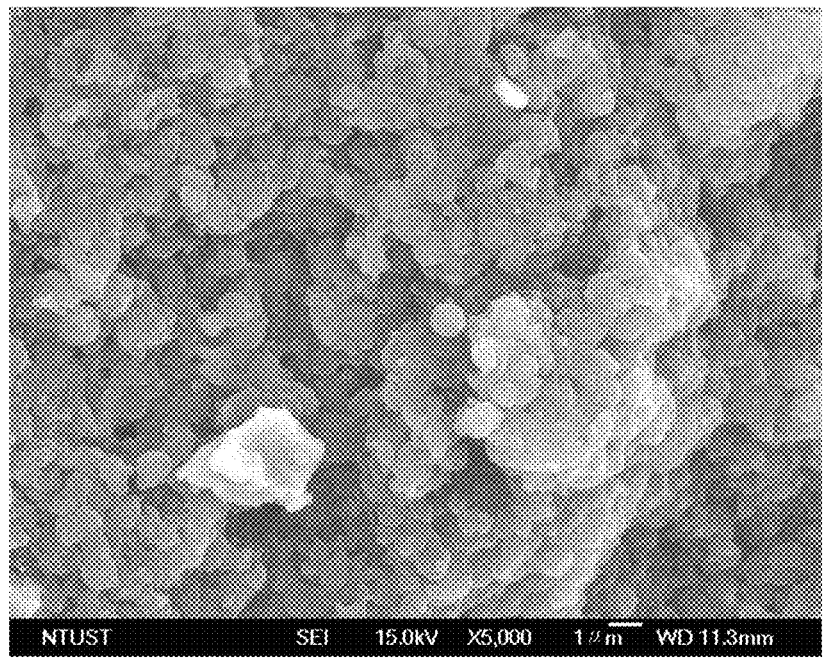
FIG. 4A is an SEM analysis result of a composite shell particle according to an embodiment of the invention.
Figure 4B:
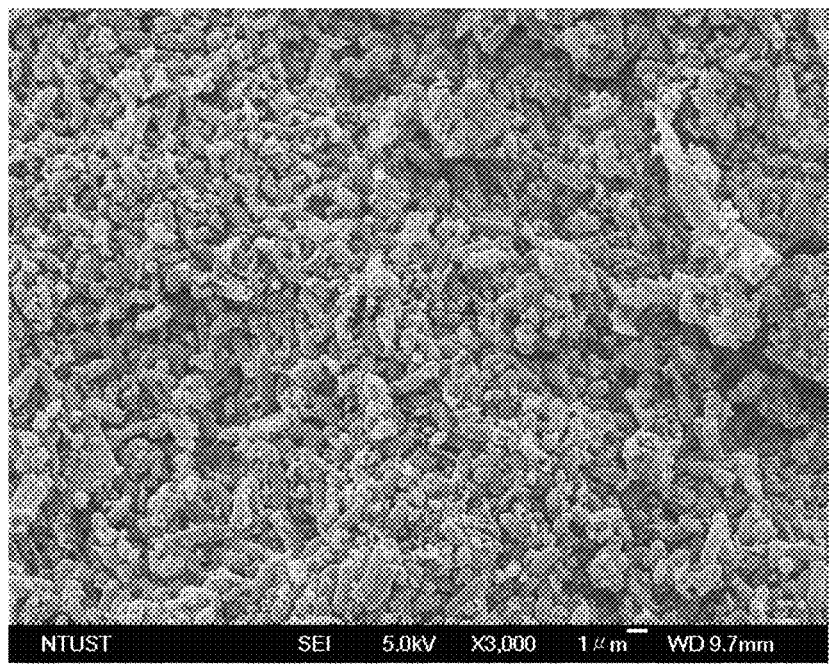
FIG. 4B is an SEM analysis result of a composite shell particle according to an embodiment of the invention.

FIG. 4A and FIG. 4B are diagrams of the SEM analysis result of a composite shell particle according to an embodiment of the invention. Referring to FIG. 4A and FIG. 4B, it may be observed from the image of the SEM analysis that the powder material has a composite shell particle having a composite shell layer that is mostly particle-shaped (FIG. 4A) and a composite shell particle having a rod-shaped composite shell layer (FIG. 4B). Each composite shell layer has a diameter of about 1 micron and a particle shell thickness of about 20 nm to 40 nm. Therefore, it may be known that air takes up most of the space inside the composite shell layer. In addition, even if the powder is compressed into a sheet by a pressure of 10 MPa, the composite shell layer may withstand this pressure without causing structural damage such as cracks and breakage. Accordingly, it is inferred that the compressive strength thereof is greater than 10 MPa.

Figure 5:
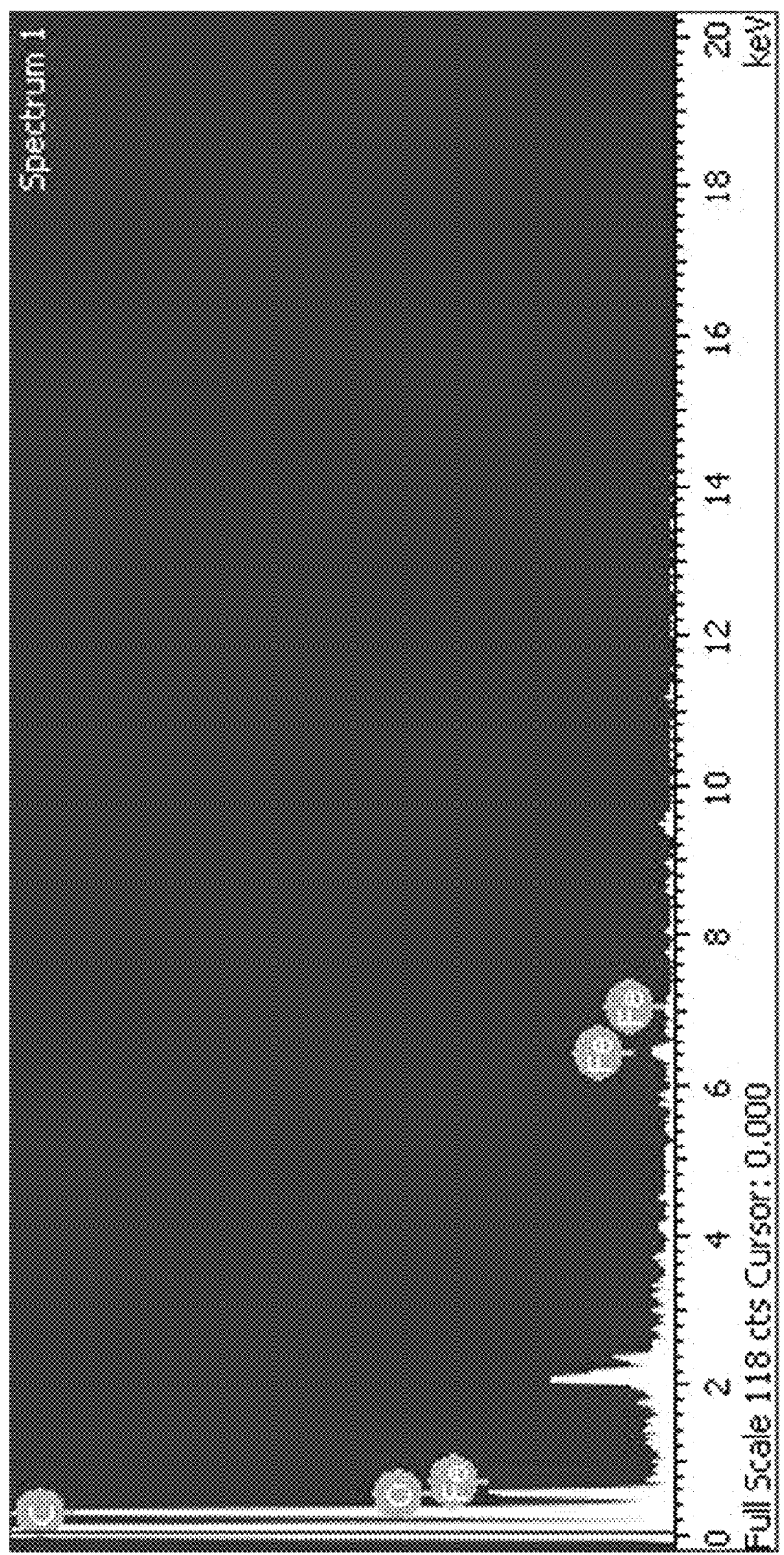
FIG. 5 is an EDS analysis result of a composite shell particle according to an embodiment of the invention.
Figure 6:
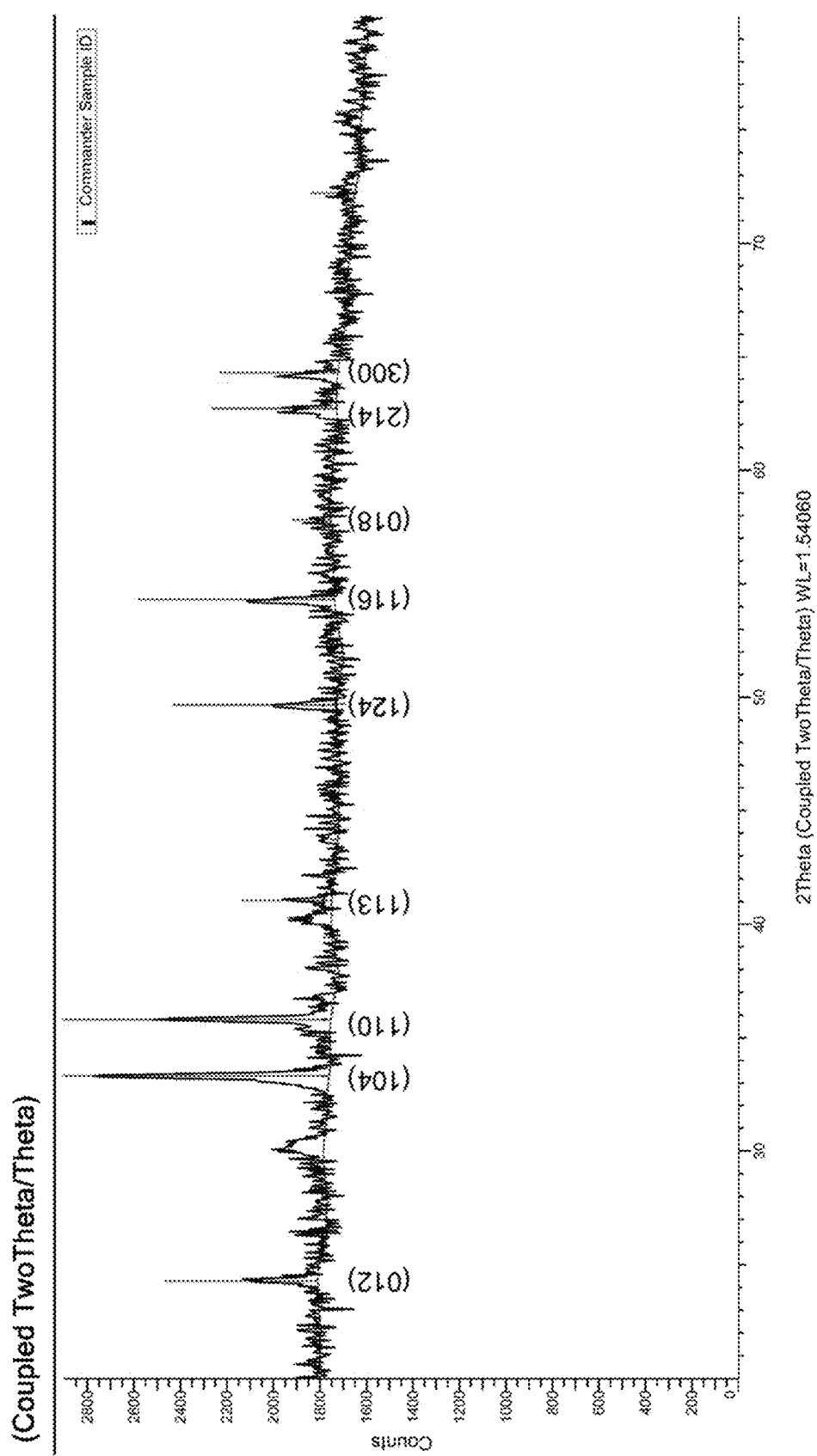
FIG. 6 is an XRD analysis result of a composite shell particle according to an embodiment of the invention.

FIG. 5 is the EDS analysis result of a composite shell particle according to an embodiment of the invention. The result of the EDS analysis indicates that the elements detected in the composite shell layer of the composite shell particle mainly include: carbon, oxygen, and iron. From this experimental result, it is confirmed that the metallic layer of the enhanced composite shell layer includes a chelate of EDTA and iron, and carbon is the main atomic composition. FIG. 6 is the XRD analysis result of a composite shell particle according to an embodiment of the invention. The XRD analysis result of the composite shell particle shows that there is a sharp peak at 2θ=33.2° and 2θ=35.8°, which is the Miller index corresponding to ferric oxide, and therefore it is confirmed that the crystal structure thereof is mainly an iron oxide of ferric oxide.

In an embodiment of the invention, the composite shell particle may be adapted to prepare a biological material such as an artificial bone material. When used as a possible material for artificial bone, the mechanical strength thereof is a very important property that affects the application range of this hollow nano shell particle. In order to confirm the structural strength of the composite shell particle of the embodiments of the invention, 0.5 g of the enhanced EDTA-iron chelate hollow nano shell particle powder was placed in a tablet mold having a diameter of 20 mm and a cross-sectional area of 3.14 cm$^2$. After compression, the size thereof was about 3 mm, and then the deformation thereof was measured by a micrometer rangefinder to obtain the pressure versus deformation diagram shown in FIG. 7.

Figure 7:
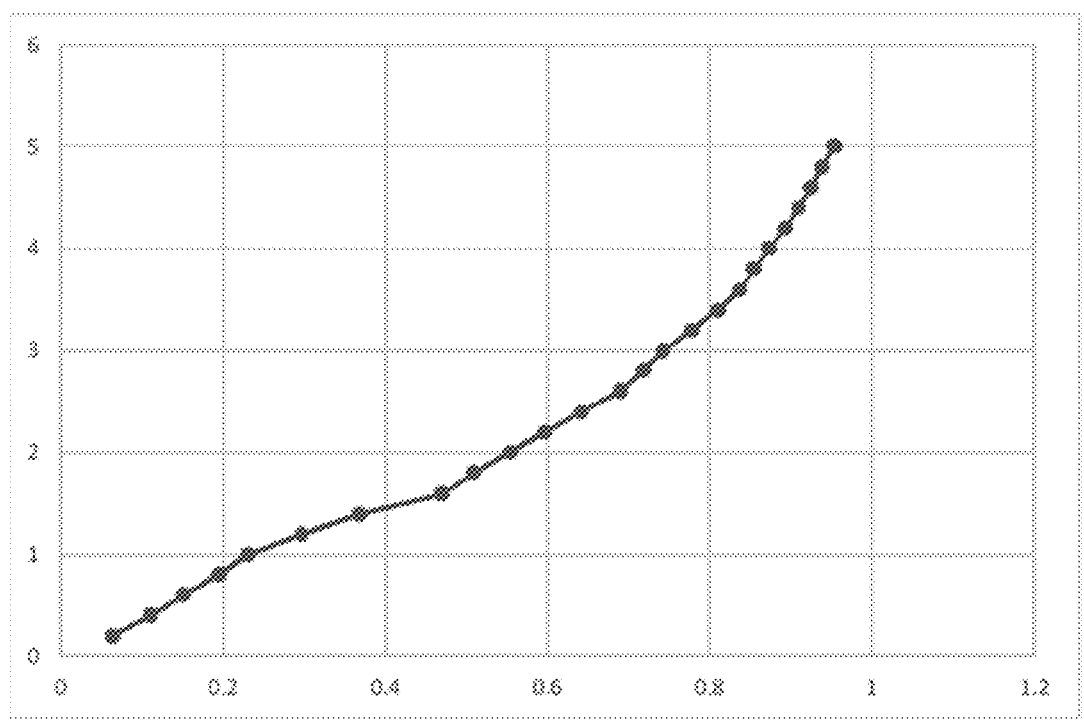
FIG. 7 is a pressure versus deformation diagram of a composite shell particle according to an embodiment of the invention.

FIG. 7 is a pressure versus deformation diagram of a composite shell particle according to an embodiment of the invention. Referring to FIG. 7, the horizontal axis is the amount of deformation (mm) and the vertical axis is the pressure (metric ton). In general, the curve of the pressure versus deformation diagram may be divided into three regions, namely linear region, plain region, and dense region. In this experiment, the upper limit of the linear region was 1.2 metric tons, and therefore the converted endpoint pressure thereof was about 37.4 MPa. Compared with the compressive strength of the trabecular bone (2 MPa to 10 MPa), the compressive strength of the composite shell particle of the EDTA-iron chelate hollow nano shell particle of the present experimental example may reach 37 MPa. Therefore, the composite shell particle of the EDTA-iron chelate hollow nano shell particle may be used as a good material for artificial bone. In addition, the endpoint pressure of the composite shell particle that was not enhanced was confirmed to be about 10 MPa by the same experiment. Therefore, it may be known that the compressive strength of the composite shell particle may be further improved by the enhancing treatment step of the invention (for example, by performing a hydration reaction or to scorch cellulose for crosslinking).

Based on the above, the composite shell particle and the manufacturing method thereof of the embodiments of the invention are suitable for the manufacture of a novel material. By the principle of microbial mineralization, a composite shell particle with low material volume occupancy and excellent mechanical properties and structural strength may be obtained, and therefore the composite shell particle may be used as a biological material. Moreover, the process of manufacturing this composite shell particle is simple, inexpensive, and easy for mass production. In addition, the composite shell particle still maintains the integrity of the dome-like structure thereof after being compressed at a pressure of 10 MPa, and the compressive strength thereof may reach 37 MPa. Therefore, the composite shell particle of the embodiments of the invention may be applied to the development of novel materials, biological materials, and related products with both excellent mechanical properties and structural strength.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A method of manufacturing a composite shell particle, comprising:
   co-culturing bacteria or algae cells together with a culture medium comprising a carbon source and a metal raw material for a period of time, and the metal raw material in the culture medium is subjected to a redox reaction induced by the bacteria or algae cells to produce a wet powder material containing composite shell particles, wherein the method further comprises, after the culturing step:
   causing an upper layer of the culture medium to form a foam; and
   separating a suspension from the foam to obtain the wet powder material,
   wherein the metal raw material is composed of a metal compound, and a metal in the metal compound is at least one selected from a group consisting of iron, molybdenum, tungsten, manganese, zirconium, cobalt, nickel, copper, zinc, and calcium, and the metal compound is at least one selected from a group consisting of metal chelates, metal oxides, metal sulfides, metal chlorides, metal selenides, metal acid salt compounds, and metal carbonate compounds;

separating the wet powder material from the culture medium;

drying the wet powder material to obtain a powder material, wherein the powder material comprises at least the composite shell particles; and placing the powder material comprising the composite shell particles in a solution or under vacuum and reacting at 0° C. to 250° C. to enhance a compressive strength of the composite shell particle.

2. The method of manufacturing the composite shell particle of claim 1, wherein the powder material comprising the composite shell particle is placed in an aqueous solution and hydrated in water at 0° C. to 100° C. for 3 days to 7 days to bond the composite shell particles to each other for enhancing the compressive strength of the composite shell particle.

3. The method of manufacturing the composite shell particle of claim 1, wherein the solution is an organic solution, and the powder material comprising the composite shell particle is placed in the solution and heated to 60° C. to 80° C., and then the solution is removed and a reaction is performed in a vacuum environment at 150° C. to 250° C. for 4 hours to 24 hours to scorch and crosslink a cellulose of a cell wall in the composite shell particle for enhancing the compressive strength of the composite shell particle.

4. The method of manufacturing the composite shell particle of claim 1, wherein the bacteria or the algae is at least one of a Gram-negative bacteria selected from *Shewanella* sp., *Pantoea* sp., *Pseudomonas aeruginosa*, *Bacillus subtilis*, and *Crustose coralline* algae.

5. The method of manufacturing the composite shell particle of claim 1, wherein the metal is iron, and the metal compound comprises a chelate of EDTA and iron, iron oxide, ferric citrate, or iron chloride.

6. The method of manufacturing the composite shell particle of claim 1, wherein in the co-culturing step, the bacteria or algae cells are subjected to a stress response such that a cell wall or a cell membrane of the bacteria or the algae forms a hollow shell, and the composite shell layer of the composite shell particle forms a hollow sphere-shaped shell or a hollow rod-shaped shell having a dome shape at two end portions.

7. The method of manufacturing the composite shell particle of claim 1, wherein the metal raw material has a concentration of 0.01 M to 0.2 M in the culture medium.

8. The method of manufacturing the composite shell particle of claim 1, wherein the powder material has a density of 420 kg/m$^3$.

9. The method of manufacturing the composite shell particle of claim 1, wherein the co-culturing step comprises: placing the bacteria or algae cells in the culture medium and culturing for a period of time under an aerobic environment at 37° C.

10. The method of manufacturing the composite shell particle of claim 1, wherein the culture medium is an LB culture medium or an M9 culture medium.

11. The method of manufacturing the composite shell particle of claim 1, wherein the co-culturing step has a culturing time of 3 days to 5 days.

12. The method of manufacturing the composite shell particle of claim 1, wherein the carbon source has a concentration of 0.01 M to 0.2 M in the culture medium.

13. A method of manufacturing a composite shell particle, comprising:

co-culturing bacteria or algae cells together with a culture medium comprising a carbon source and a metal raw material for a period of time, and the metal raw material in the culture medium is subjected to a redox reaction induced by the bacteria or algae cells to produce a wet powder material containing composite shell particles, wherein the metal raw material is composed of a metal compound, and a metal in the metal compound is at least one selected from a group consisting of iron, molybdenum, tungsten, manganese, zirconium, cobalt, nickel, copper, zinc, and calcium, and the metal compound is at least one selected from a group consisting of metal chelates, metal oxides, metal sulfides, metal chlorides, metal selenides, metal acid salt compounds, and metal carbonate compounds;

separating the wet powder material from the culture medium, wherein the separating step comprises:
centrifuging the culture medium to form a precipitate; and
separating the precipitate from the centrifuged cultured medium to obtain the wet powder material;

pulverizing the wet powder material to form a pre-powder material, wherein the pulverizing step comprises: ultrasonically oscillating the wet powder material;

drying the pre-powder material to obtain a powder material, wherein the powder material comprises at least the composite shell particles; and placing the powder material comprising the composite shell particles in a solution or under vacuum and reacting at 0° C. to 250° C. to enhance a compressive strength of the composite shell particle.

14. The method of manufacturing the composite shell particle of claim 13, further comprising, after the pulverizing step: washing the pre-powder material with a solvent at least once.

15. A method of manufacturing a composite shell particle, comprising:

co-culturing bacteria or algae cells together with a culture medium comprising a carbon source and a metal raw material for a period of time, and the metal raw material in the culture medium is subjected to a redox reaction induced by the bacteria or algae cells to produce a wet powder material containing composite shell particles, wherein the metal raw material is composed of a metal compound, and a metal in the metal compound is iron, and the metal compound is at least one selected from a group consisting of iron chelates, iron oxides, iron sulfides, iron chlorides, iron selenides, iron acid salt compounds, and iron carbonate compounds;

separating the wet powder material from the culture medium;

drying the wet powder material to obtain a powder material, wherein the powder material comprises at least the composite shell particles; and placing the powder material comprising the composite shell particles in a solution or under vacuum and reacting at 0° C. to 250° C. to enhance a compressive strength of the composite shell particle.

16. The method of manufacturing the composite shell particle of claim 15, further comprising, after the culturing step:

causing an upper layer of the culture medium to form a foam; and separating a suspension from the foam to obtain the wet powder material.

17. The method of manufacturing the composite shell particle of claim 15, wherein the bacteria or the algae is at least one of a Gram-negative bacteria selected from *Shewanella* sp., *Pantoea* sp., *Pseudomonas aeruginosa*, *Bacillus subtilis*, and *Crustose coralline* algae.

\* \* \* \* \*